US008529970B2

(12) United States Patent
Brown et al.

(10) Patent No.: US 8,529,970 B2
(45) Date of Patent: *Sep. 10, 2013

(54) HIGH UNSAPONIFIABLES AND METHODS OF USING THE SAME

(75) Inventors: James H. Brown, Scottsdale, AZ (US); Lee Roy Copeland, Show Low, AZ (US); Robert Kleiman, Mesa, AZ (US); Melanie K. Cummings, Lake Elsinore, CA (US); Sambasivarao Koritala, Sun Lakes, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/097,751

(22) Filed: Apr. 29, 2011

(65) Prior Publication Data

US 2011/0293544 A1 Dec. 1, 2011

Related U.S. Application Data

(63) Continuation of application No. 12/203,004, filed on Sep. 2, 2008, now Pat. No. 7,955,611, which is a continuation-in-part of application No. 10/611,775, filed on Jun. 30, 2003, now abandoned, and a continuation-in-part of application No. 09/478,071, filed on Jan. 3, 2000, now Pat. No. 7,435,424.

(51) Int. Cl.
  *A61K 36/00* (2006.01)
(52) U.S. Cl.
  USPC .......... 424/776; 424/59; 424/63; 424/64; 424/65; 424/70.1; 424/70.9; 424/73; 424/76.1; 424/405; 424/406; 514/844; 514/845; 514/846; 514/847; 514/848; 514/858; 514/859; 514/860; 514/861; 514/862; 514/863; 514/864; 514/865; 514/871; 514/880; 514/881; 514/886; 514/887; 514/918; 514/919; 514/947; 514/969
(58) Field of Classification Search
  None
  See application file for complete search history.

(56) References Cited

U.S. PATENT DOCUMENTS

| 2,350,082 A | 4/1942 | Taussky |
| 3,217,046 A | 11/1965 | Mikolajczak |

(Continued)

FOREIGN PATENT DOCUMENTS

| EP | 0069946 | 1/1983 |
| EP | 482344 A1 | 4/1992 |

(Continued)

OTHER PUBLICATIONS

Jojoba Happenings, article, 1985, 7 pages, USA.

(Continued)

*Primary Examiner* — Neil Levy
(74) *Attorney, Agent, or Firm* — The Noblitt Group, PLLC (57) ABSTRACT

Materials with high levels of unsaponifiable matter, such as extracts from plants, produce hydrolysates with unique properties. Properties that are sought in traditional saponification of natural oils are a result of low levels of unsaponifiables. These properties include high levels of aqueous surfactant activity, water-solubility or ready water-dispersability, activity as foaming agents, and the like. An objective of traditional saponification processes is to increase the water-solubility and surfactant activity of naturally occurring materials. It has been found that the application of a hydrolysis process to materials, particularly materials with a high level of unsaponifiables (e.g., at least 6 weight percent of the material), produces a product with properties significantly different from those products resulting from the conventional saponification of materials with less than 6 weight percent of unsaponifiables. The resulting hydrolysates from the practice of the present invention are substantive, resisting both physical and aqueous-based removal from skin and hair, exhibit a very unique surfactant property, and are not foaming agents with water. Hydrolysates according to the present invention may thus be used to enhance the performance of cosmetics and pharmaceuticals. These hydrolysates can be bioactive agents and alternative natural carrying agents for topical application of materials, particularly for application of materials to the skin or hair of subjects, and provide a substantive support for the materials carried.

7 Claims, 7 Drawing Sheets

(56) References Cited

U.S. PATENT DOCUMENTS

| | | | |
|---|---|---|---|
| 3,226,406 | A | 12/1965 | Miwa et al. |
| 3,460,387 | A | 8/1969 | Brown |
| 3,849,323 | A | 11/1974 | Hollinshead |
| 4,324,802 | A | 4/1982 | Koulbanis et al. |
| 4,329,298 | A | 5/1982 | Brown et al. |
| 4,356,197 | A | 10/1982 | Devitt et al. |
| 4,360,387 | A | 11/1982 | Brown et al. |
| 4,393,043 | A | 7/1983 | Koulbanis et al. |
| 4,437,895 | A | 3/1984 | Koulbanis et al. |
| 4,664,914 | A | 5/1987 | Stillman |
| 4,812,253 | A | 3/1989 | Small et al. |
| 5,159,124 | A | 10/1992 | Bertholet |
| 5,750,563 | A | 5/1998 | Honda |
| 5,928,659 | A | 7/1999 | Moy |
| 6,117,119 | A | 9/2000 | Gould |
| 6,265,370 | B1 | 7/2001 | Newbegin |
| 6,280,746 | B1 | 8/2001 | Arquette et al. |
| 7,250,174 | B2 | 7/2007 | Lee et al. |
| 7,393,528 | B2 * | 7/2008 | Tvedten .................... 424/94.63 |
| 7,435,424 | B1 * | 10/2008 | Copeland et al. ............. 424/406 |
| 7,955,611 | B2 * | 6/2011 | Brown et al. ................. 424/405 |
| 2004/0265343 | A1 | 12/2004 | Hill |
| 2007/0004599 | A1 | 1/2007 | Darbha |
| 2008/0254150 | A1 * | 10/2008 | Rheins et al. ................. 424/725 |
| 2000/0041868 | | 2/2009 | Brown |

FOREIGN PATENT DOCUMENTS

| | | |
|---|---|---|
| EP | 689828 A1 | 1/1996 |
| FR | 7930956 A | 6/1981 |
| FR | 94/00301 | 9/1994 |
| FR | 2762512 A | 10/1998 |
| FR | 2000-56500 | 2/2000 |
| GB | 513774 | 10/1939 |
| GB | 558820 A | 1/1944 |
| GB | 755114 A | 8/1956 |
| GB | 1520523 | 8/1978 |
| IN | 178981 | 8/1997 |
| IN | 179013 | 8/1997 |
| JP | 61-210054 | 9/1986 |
| JP | 61207313 | 9/1986 |
| JP | 62-152103 | 12/1988 |
| WO | 0121605 A2 | 3/2001 |
| WO | 01/49257 A1 | 7/2001 |
| WO | 2007143672 A1 | 12/2007 |
| WO | 2008/121355 A1 | 10/2008 |

OTHER PUBLICATIONS

Jojoba Happenings, article, 1987, 12 pages, vol. 15 No. 4, USA.
Jojoba Happenings, article, Mar.-Apr., 12 pages, vol. 12 No. 2, USA.
Jojoba Happenings, article, 1987, 12 pages, vol. 15 No. 5, USA.
Susan Miller Cavitch, The Natural Soap Book—Making Herbal and Vegetable-Based Soaps, book, 1995, 98 pages, Storey Publishing, USA.
Susan Miller Cavitch, The Soapmakers Companion, book, 1997, 147 pages, Storey Publishing, USA.
Supplement to Arid Lands Resource Information Paper No. 5/Jojoba: An Annotated Bibliographic Update , paper, 1978, 4 pages, USA.
Richard S. Gelger and Mary Beck Moser, Sen Indian Pharmacopoeia, article, 1974, pp. 415-436.
Journal of the American College of Toxicology, Final Report on the Safety Assessment of Jojoba Oil and Jojoba Wax, article, 1992, 18 pages, Mary Ann Liebert, Inc Publishers.
Report of an ad hoc panel of the Advisory Board re Jojoba New Crop for Arid Lands, New Raw Material for Industry, report, 1985, 4 pages, National Academy Press.
Jerome Smith, Jojoba: The Super Bean of the Future Part 1, article, 1982, 4 pages, Adam Smith Publishing, USA.
Jojoba: Feasibility for Cultivation on Indian Reservations in the Sonoran Desert Region, article, 1977, 7 pages, USA.
Jojoba: A Wax-Producing Shrub of the Sonoran Desert, article, 1974, 2 pages, USA.
Jojoba Happenings, Jojoba Soapmaking, article, 1992, 1 page, USA.
Gottschalck and Bailey, International Cosmetic Ingredient Dictionary and Handbook, book, 2012, 5 pages, Thirteenth Edition—vol. 1, Personal Care Products Council, USA.
Gottschalck and Bailey, International Cosmetic Ingredient Dictionary and Handbook, book, 2012, 4 pages, Thirteenth Edition—vol. 2, Personal Care Products Council, USA.
Gottschalck and Bailey, International Cosmetic Ingredient Dictionary and Handbook, book, 2012, 33 pages, Thirteenth Edition—vol. 3, Personal Care Products Council, USA.
Gottschalck and Bailey, International Cosmetic Ingredient Dictionary and Handbook, book, 2012, 4 pages, Thirteenth Edition—vol. 4, Personal Care Products Council, USA.
Tiffany Oliphant, Douglas Gilmore and Robert Harper, Hydrolyzed Jojoba Esters to Potentiate Glycerin Moisturization, article, 2008, 6 pages, USA.
Oils and Fats in India, Inform newsletter, Mar. 2009, 2 pages, vol. 20(3).
Abbot, Nakamura, Buchholz, Wolf, Palmer, Gasdorf, Nelson, and Kleiman, Process for Making Animal Fee and Protein Isolates from Jojoba Meal, article, 1991, pp. 1488-1493, USA.
Arquette, Bailyn, Palenske. Bergman and Rheins, Non-comedogenic and hypoallergenic properties of jojoba oil and hydrogenated jojoba oil, article, 1998, pp. 377-383, USA.
Ashour, Ayoub, Singab, Al-Azizi, Chemical Compostion and Anti-Inflammatory Activity of the Natural Wax Isolated from Egyptian Jojoba, article, 1 page, Cairo, Egypt.
S. Binman, S. Belfer and A. Shani, Functionaliztion at the Double-Bond Region of Jojoba Oil, article, 1996, pp. 1083-1095, Israel.
J. Bousson-Breysse, M. Farines and J. Soulier, Jojoba Wax: Its Esters and Some of its Minor Components, article, Sep. 1994, pp. 999-1003, Perpignan, France.
Paul A. Cadicamo and James J. Cadicamo, A Second Study of Jojoba Oil, Its Derivatives and Other Cosmetic Oils, article, 1983, pp. 36-38, USA.
Paul A. Cadicamo and James J. Cadicamo, A Study of Jojoba Oil, its derivative and other cosmetic oils, article, 1982, pp. 67-70, vol. 97, Allured Publishing Corp., USA.
M.S. Christensen and E.W. Packman, Skin Surface Softening Effects of Jojoba and its Derivatives, article, pp. 298-306, USA.
M.L. Tonnet, R.L. Dunstone and A. Shani, A Rapid Micromethod for the Quantitative Analysis of Jojoba Wax and its Components, article, Jun. 1984, pp. 1061-1065, Israel.
Sara P. Fore, Frank C. Magne, and W.G. Bickford, Epoxidized jojoba oil as a stabilizer for vinyl chloride containing plastics, article, 1958, pp. 469-472, vol. 35, USA.
Arjeh B. Galun, Eleonora Shaubi, Arie Markus, Sarina Grinberg, and Jacob Zabicky, Photosensitized cis-trans Isomerization of Jojoba Wax, article, 1983, pp. 102-103, Israel.
J. Graille, M. Pina, D. Ploch, Routine Analysis of Jojoba Wax Fatty Acids and Alcohols, article, 1986, pp. 111-117, Cedex, France.
J. Hamilton, M. Yaquob Raie and Thomas K. Miwa, Structure of the Alcohols Derived from Wax Esters in Jojoba Oil, article, 1975, pp. 92-96, North-Holland Publishing Company.
Lemoyne Hogan, New Crop for Arid Regions? Jojoba, article, 1978, pp. 14-16.
Arieh Kampf, Sarina Grinberg, and Arjeh GaLun, Oxidative Stability of Jojoba Wax, article, 1985, pp. 246-248, Israel.
Nestor B. Knoepfler and H.L.E. VIX, Review of Chemistry and Research Potential of Simmondsia Chinensis (Jojoba) Oil, article, 1958, pp. 118-121, vol. 6 No. 2, USA.
P.S. Landis and R.H. Craver Sr., Solubility of Jojoba Oil in Organic Solvents, article, pp. 1879-1880, USA.
S. Magdassi and A. Shani, Surface Activity of Quaternary Ammonium Salts Derived from Jojoba Oil, article, 1990, pp. 605-606, vol. 67 No. 9, Israel.
Thomas K. Miwa, Jojoba Oil Wax Esters and Derived Fatty Acids and Alcohols: Gas Chromatographic Analyses, article, 1970, pp. 259-264, USA.
Thomas K. Miwa, Structural Determination and Uses of Jojoba Oil, article, 1984, pp. 407-410, vol. 61 No. 2, USA.
Hal C. Purcell, Thomas P. Abbott, Ronald A. Holser, and Bliss S. Phillips, Simmondsin and wax ester levels in 100 high-yielding jojoba clones, article, 2000, USA.

Arnon Shani, Funcationalization a the Double Bond Region of Jojoba Oil: I. Bromine Derivatives, article, 1981, pp. 845-850, Israel.
N. Taguchi and T. Kunimoto, Toxicity studies on jojoba oil for cosmetic uses, article, 1977, pp. 53-62, vol. 92, Tokyo, Japan.
M. Van Boven, P. Daenens, K. Maes, and M. Cokelaere, Content and Composition of Free Sterols and Free Fatty Alcohols in Jojoba Oil, article, 1997, pp. 1180-1184, Kortrijk, Belgium.
Jaime Wisniak and Michael Holln, Hydrogenation of Jojoba Oil, article, 1975, pp. 226-231, vol. 14 No. 4, Israel.
Jaime Wisniak and Pnina Alfandary, Sperm Whale Oil Replacements from Halogenation of Jojoba Oil, article, 1979, pp. 358-364, Israel.
Jaime Wisniak, The Chemistry and Technology of Jojoba Oil, book, 1987, 143 pages, American Oil Chemists' Society, USA.
D.M. Yermanos, Composition of Jojoba Seed during Development, article, 1974, pp. 115-117, USA.
D.M. Yermanos and C.C. Duncan, Quantitative and Qualitative Characteristics of Jojoba Seed, article, Feb. 1976, pp. 80-83, USA.
Jacob Zabicky and Moshe Mhasalkar, Diozonide of Jojoba Wax as Intemediate for Synthesis, Jan. 1986, pp. 1547-1550, vol. 63 No. 12, Israel.
Subject: Transesterification of Jojoba Esters, information sheet, 1 page.
Thomas Benigan and Anthony Berbiscar, Decoloration and Purification: Treatments can overcome jojoba oil 'throw', article, p. 29.
Hydrogenation and Deodorization, information sheet, Mar. 11, 1991, 1 page.
Brochure for FloraEsters, information sheet, 3 pages.
Brochure—Floratech product overview, information sheet, 3 pages.
J. Brown and K. Dwyer, The Jojoba Potential: An Overview, article, pp. 343-353.
James H. Brown, Jojobutter-51—A Primary Dermal Irritation Study in Rabbits, article, 2 pages.
Desert Whale—Certificate of Analysis for Aqua-Sol PEG 120, information sheet, 4 pages.
Desert Whale—Material Safety Data Sheet for jojoba, hydrogenated, information sheet, 3 pages.
Jojoba Oil and derivatives, information sheet, 1 page.
Anthony J. Berbiscar, Jojoba Alcohol for Topical Antiviral Treatment, provisional patent application, May 28, 1998.
Presentation Guide for Floratech meeting overheads production script for Florabeads, presentation, 5 pages.
Presentation Guide for Floratech Meeting overhead production script for Florasun, presentation, 9 pages.
Presentation agenda for Floratech Annual marketing matter and dinner in Paris, presentation, Apr. 4, 1995, 5 pages.
Notes re Meeting Book Layout and contents draft for Floratech agents 3rd annual worldwide marketing and tecnical meeting, presentation, Mar. 7, 1995, 2 pages.
Transesterification of Jojoba Esters as a Source of New Wax Esters—84th AOCS Annual Meeting & Expo by J. Arquette, J. Covey and R. Kleimman, presentation, Apr. 29, 1993, 19 pages.
The Jojoba Industry—A status and Update, presented by J. Brown, presentation, Sep. 7, 1986, 43 pages.
Paul A. Cadicamo and James J Cadicamo, A Second Study of Jojoba Oil, its derivatives and other cosmetic oils, article, 1983, pp. 36-38.
Inform—Jojoba growers aiming at cosmetic markets, article, Apr. 1996, pp. 420,422,425, vol. 7, No. 4, Italy.
Pete Dolack, Chemical Marketing Reporter—Jojoba Producers form a marketing cooperative, article, Jan. 8, 1946, 1 page.
Arnon Shani, The struggles of jojoba, article, May 1995, pp. 49-54.
James Brown, David Palzkill, Carole Whittaker, The Jojoba Industry, report, 1994, pp. 1-13.
Arnon Shani, Jojoba—Literature, Reviews, Scientific Papers, Jojoba Utilization—Patents and selected articles, information sheet, pp. 1-19.
Paul Cadicamo and James Cadicamo, NewRelease—Jojoba Growers & Processors Inc.—A Second Study of Jojoba Oil, its derivatives and other cosmetic oils, Information sheet, Jun. 1983, 1 page.
Roberta Wilson, Jojoba and Jojoba Derivatives for formulating cosmetics, article, Nov. 1992, pp. 43, 46, 50, 53.

Barbara Fitch Naumann, Journal of the American Oil Chemists Society, Jan. 1983, Jojoba Desert Shrub to Commercial crop, publication, Jan. 1983, vol. 60 No. 1, 14 pages, Journal of The American Oil Chemists Society.
Giovanni Mignoni, Agro-Industry Hi-Tech articles titled The Jesuits and the jojoba, article, pp. 9-16.
Agro-Industry Hi-Tech articles titled Jojoba, Agronomicals characteristics and industrial applications, article, pp. 17-21.
J. Radisson, Agro-Industry Hi-Tech articles titled Technology transfer to imporve productivity and efficiency in animal production, East—West business opportunities, article, 1930, 2 pages, Arizona.
John G. Reinhardt and James Brown, Jojoba Oil and Derivative Safety and Applications in Cosmetics, presentation, 40 pages.
David A. Palzkill, Mohamed H. Younes, Lemoyne Hogan, HortScience article: AT-1310, AT-1487, and AT-3365: Clonal Jojoba Germplasm Selected for Horticultural Use, article, Jun. 1989, pp. 526-527, vol. 24(3).
J. Busson-Breysse, M. Farines and J. Soulier, Jojoba Wax: Its Esters and Some of its Minor Components, article, Sep. 1994, pp. 999-1002, France.
Paul Cadicamo and James Cadicamo, NewsRelease Jojoba Growers & processors—A Second Study of Jojoba Oil, its derivatives and other cosmetic Oils, information sheet, Jun. 1983, 2 pages.
Arnon Shani, Chemicals and Technological aspects of jojoba wax and its derivatives, Jul. 1996, pp. 71-77, vol. 28 No. 3, Israel.
Wax Ester Combinations of jojoba oil, information sheet, 3 pages.
International Flora Technologies, Refined jojoba oil procedure, information sheet, Sep. 22, 1993, 1 page.
Structural Determination and Uses for Jojoba Oil, article, pp. 407-410.
N. Sanchez, M. Martines, J. Aracil and A. Corma, Synthesis of Oleyl Oleate as a jojoba oil analog, Nov. 1992, pp. 1150-1153, vol. 69 No. 11, Israel.
Thomas K. Miwa, Chemical aspects of jojoba oil a unique liquid wax from desert shrub, article, 3 pages.
Ralph T. Holman, Progress in the Chemistry of Fats and other Lipids—Jojoba Oil and Derivatives, publication, 1977, 27 pages, Pergamon Press, England.
James Brown, David Palzkill and Carole Whittaker, The Jojoba industry, 1994, a status and updated, report, 1994, 10 pages.
Obesity Control Dog Food, report, 13 pages.
Total Synthesis of Simmondsin, article, 1997, pp. 588-590.
Noritaka Chida, Ken Yamada and Seiichiro Ogawa, Synthesis and Absolute Configuration of the naturally occurring Cyano glucoside simondsin, 1992, pp. 1131-1137, Japan.
Indentification of jojoba compents, information sheet, 1 page.
Random.xls; Feb. 25, 1993, information sheet, 1 page.
Page from publication re unit processes in organic synthesis, publication, 1935, p. 386-387.
Kevin F. Gallagher, Hydrolyzed Vegetable proteins: A formulators Guide (part 1), article, Aug. 1991, 8 pages.
Manuscript Peer Review for Saponification of *Lesquerella fendleri* oil in methanolic alkali by K. Carlson and R. Kleiman, information sheet, 20 pages.
Cecil R. Smith, Jr., Unusual seed oils and their fatty acids, 1979, pp. 29-47, USA.
Kenneth D. Carlson and Robert Kleiman, Saponification of *Lesquerella fendleri* oil in methanolic alkali, report, pp. 1-19.
Study of Cosmetic Oils, Derivatives and Other Cosmetic Components, report, 8 pages.
Susan J. Ainsworth, Personal Care Products—Demand for more creative ingredients rejuvenates an aging market, Apr. 4, 1994, pp. 38, 40-49.
Interesterify Jojoba, project No. 77-90635A, information sheet, Mar. 12, 1991, 3 pages.
Process Report—Refine and Bleach Crude jojoba oil, information sheet, Sep. 26, 1995, 4 pages.
POS Newsletter—exPOSure—a publication of patents for the agrifood industry, article, Sep. 1990, pp. 1-6, vol. 1 No. 2.
Process Directive to Process Bleach Jojoba Oil, information sheet, Sep. 21, 1993, 2 pages.
Process Directive to Process Deodorize Jojoba Oil, information sheet, Sep. 22, 1993, 1 page.

Process Directive to Process Hydrogenate Jojoba, information sheet, Sep. 23, 1993, 2 pages.

Process Directive, Process: Deodorize Jojoba Stearine 93-F, Sep. 23, 1993, 2 pages.

Ralph T. Holman, Progress in the Chemistry of Fats and other Lipids, 1977, 54 pages, vol. 15 No. 3, Pergamon Press, Great Britian.

P.M. Daugherty, H.H. Sineath, and T.A. Wastler, Industrial Raw Materials of Plant Origin; A Survey of *Simmondsia chinensis* (Jojoba), article, 1953, 36 pages, vol. 15 No. 13, USA.

Increased Sunscreen Retention with Floraesters K-20W & Floraesters K-100, information sheet, 2010, 1 page.

Formulating with K-Series K20W versus K100, information sheet, May 12, 2010, 2 pages.

Tiffany Oliphant, David Ashley, Chad Dubbelde, Doug Gilmore and Gina Bowser, FloraTech—Clinical Assessment of Jojoba Oil Derviatives (jojoba hydrolysate, jojoba esters, jojoba alcohol, and isopropyl jojobate) in a gel sanitizer in healthcare workers with acquired occupations hand dermatitis—a pilot study, report, Apr. 1, 2009, 14 pages, USA.

Tiffany Oliphant and David Ashley, FloraTech—Clinincal and bioinstrumental evaluation of extended moisturization skin care lotion(s) a controlled study, report, Mar. 4, 2009, 17 pages, USA.

FloraTech—Clinical and bioinstrumental evaluation of extended moisturization skin care lotion(s) (glyceral & floraesters k-20w jojoba) a controlled use study, report, Apr. 15, 2008, 11 pages, USA.

Tiffany Oliphant, David Ashley, Chad Dubbelde, Doug Gilmore and Gina Bowser, FloraTech—A clinical evaluation of an anti-aging cream product on multiple skin condition parameters, report, Mar. 9, 2009, 17 pages, USA.

Tiffany Oliphant and David Ashley, FloraTech—An evaluation of multiple scalp and hair parameters of naive-american hair using a hair relaxer product formulated with jojoba oil derivatives: a split scalp pilot study, report, Mar. 4, 2009, 12 pages USA.

FloraTech—The role of floraesters k-20w jojoba in enhancing fragrance fixation on hair following treatment with supplanted shampoo and conditioner products, report, Apr. 15, 2008, 7 pages USA.

FloraTech—Clinical and bioinstrumental evaluation of extended moisturization skin care lotion(s) (glycerol/diglycerol & floraesters k-20w jojoba): a controlled use study, report, Aug. 7, 2008, 14 pages USA.

Lawrence A Rheins and Brooke D Marshall, Clinical and Sensorial assessement of multiple alcohol hand sanitizers: a pilot study, report, 2008, 12 pages USA.

FloraTech—Clinical and bioinstrumental evaluation of extended moisturization skin care lotion(s) (8% & 15% glycerol & k-20w) a controlled use study, report, Apr. 16, 2008, 14 pages USA.

FloraTech—Evaluation of alcohol hand sanitizers on SLS inducted irritant dermatitis: mitigation or exacerbation of cutaneous inflammation plus biopsy: a controlled use study, report, Apr. 16, 2008, 12 pages USA.

Lawrence A Rheins and Brooke D Marshall, Sensorial and Clinical evaluations of five alcohol hand sanitizers: Final report, report, 2008, 20 pages USA.

FloraTech—clinical and bioinstrumental evaluation of extended moisturization in a commercial liquid hand soap and body wash: a controlled use study, report, Apr. 16, 2008, 16 pages USA.

Tiffany Oliphant and David Ashley, FloraTech—The role of hydrolyzed jojoba derivatives on multiple skin conditions in hispanic and african american-skin types, report, Mar. 4, 2009, 12 pages USA.

FloraTech—Effect of Jojoba-supplemented hand sanitizer on skirt moisturization in subjects with dry skin: a controlled study, report, Jun. 25, 2009, 12 pages USA.

FloraTech—Extended Skin Moisturization with glycerin and floraesters K-20W in subjects with dry skin: a controlled study, report, Jun. 25, 2009, 14 pages USA.

FloraTech—Depositions and Substantivity of Floraesters K-20W Jojoba and Floraesers K-100 Jojoba: A Controlled Study, report, Sep. 16, 2009, 13 pages USA.

FloraTech—Evaluation of Multiple Effects of a Body Wash containing Floraesters K-100 Jojoba and Florasolvs PEG-16 Macadamia on Normal skin: A Consumer Use Study, report, Feb. 16, 2010, 11 pages.

FloraTech—Evaluation of moisturization and skin surface effects of a body wash containing floraesters k-100 jojoba and florasolvs PEG-16 macadamia in normal subjects with dry skin: A controlled study, report, Oct. 14, 2009, 13 pages.

FloraTech—Sunscreen active retention with floraesters k-20w jojoba and floraesters k-100 jojoba: a controlled study, report, Jan. 13, 2010, 17 pages.

FloraTech—Depositin and Conditioning Effect of Floraesters K-100 Jojoba: a hair tress study, report, Oct. 27, 2009, 14 pages.

FloraTech—effect of hydrolyzed jojoba-supplemented, nonwoven wipes on skin hydratin in subjects with dry skin: a controlled study, report, Mar. 8, 2010, 11 pages.

FloraTech—Clinical assessment of jojoba oil derivates in a gel sanitizer versus a currently marketed hand sanitizer to improve moderate irritant hand dermatitis with repeated use, report, Nov. 6, 2008, 37 pages.

Floratech—Deposition of Floraesters k-20w jojoba and floraesters k-100 jojoba, floraesters k-20w and k-100 deposition retention exceeds that of petroleum, information sheet, 2009.

Floratech—Increased skin hydration with floraesters k-20w jojoba/ hand sanitizer, Floraesters k-20w increases skin hydration when included in a hand sanitizer with glycerin, information sheet, 2009.

Floratech—Increased skin hydration with floraesters k-20w jojoba plus glyercin, floraesters k-20w in the presence of glycerin products skin hydration levels equal to curel, information sheet, 2009.

Floratech—Increased skin hydration with floraesters k-100 jojoba/ body wash, Floraesters k-100 increases skin hydration when used in a body wash formulation with glycerin, information sheet, 2009.

Floratech—Reducted hair breakage and reduced comb force with floraesters k-100 jojoba, floraesters k-100 jojoba reduces comb force, reduces breakage, and enhances comsumer perception by improving damaged hair, information sheet, 2010.

Floratech—Increased skin hydration with floraesters k-20w & floraesters k-100/hydro-alcoholic nonwoven wipes, Floraesters k-20w jojoba & floraesters k-100 jojoba increases skin hydration when included in a nonwoven wupe that delivers a hydro-alcoholic sanitizing formula containing glycerin, information sheet, 2010.

Floratech—Increased sunscreen retention with floraesters k-20w & floraesters k-10, floraesters k-20s jojoba & floraesters k-100 jojoba increases the retention of sunscreens on the skin post-water immersion compared to a known fixative ingredient, information sheet, 2010.

Floratech—Enhanced skin feel with florasolvs PEG-16 macadamia and floraesters k-100 jojoba/body wash, Florasolv PEG-16 macadamia and floraesters k-100 jojoba enhance skin feel when uesd in a body wsh formulation, information sheet, 2010.

Floratech—Increased consumer preference with florasolv PEG-16 macadamia/body wash, florasolv PEG-16 increases consumer preference with used in a body wash formulation, information sheet, 2010.

Jaini Meyer, Brooke Marshall, Maximo Gacula, Lawrence Rheins, Evaluation of additive effects of hydrolyzed jojoba esters and glycerol: a preliminary study, study, 2008, pp. 268-274.

Grace Hastings, Brooke Marshall, Gina Bowser, and Lawrence Rheins, Clinical Evaluation of Jojoba derivatives on hair and scalp conditioning for individuals with afro-ethic hair: a preliminary study, study, Jun. 8, 2008, 21 pages.

Lawrence A. Rheins, Mary F. Fredenberg, Brook Marshall, Grace Hastings, John Hill, and David Ashley, The role of hydrolyzed jojoba esters complex in an alcohol gel sanitizer on the skin condition of health care workers (HCW) with chronic hand dermatitis, study, 5 pages.

Tiffany Oliphant and Robert Harper, Hydrolyzed jojoba esters offer enhanced skin care, article, 2 pages.

The Role of Hydrolyzed jojoba esters as a unique botantical technology for long-acting moisturization, brochure, Mar. 2009, 4 pages.

Beneficial effect of incorporating hydrolyzed jojoba esters into skin care products, brochure, Dec. 2009, 4 pages.

Reducing hair damage with the use of hydrolyzed jojoba esters in a hair conditioner formula, brochure, Nov. 2009, 4 pages.

Retention of Sunscree actives is improved in formulats containing hydrolyzed jojoba esters as measured by ATR-FT IR, brochure, Sep. 2009, 4 pages.

Evaluation of a sample of Floraesters k-20w jojoba, study, Aug. 25, 1999, 6 pages.

Intenational Research Services Inc—A study to assess the skin sensitization potential of two products when applied to the skin of 100 healthy human sublets in a shared panel assay, study, Dec. 20, 2006, 61 pages.
Test Results on safety of jojoba oil to be used for cosmetics by masayuki taguchi technical division, report, Mar. 1976, 2 pages, Japan.
K-80 Compatability Study Results, study, Feb. 11, 1999, 3 pages.
Liquefying Cleaning Creams, article, 2 pages.
Floratech—Third Annual worldwide marketing and techinical meeting, Paris, France, presentation, Apr. 4, 1995, 117 pages.
Presentation Guide for Floratech Meeting overheads for martketing and sales discussions and book reprints, presentation, 6 pages.
AG Vereshchagin, Occurrence or Lipophilic Micellae Formed by Fatty Alcohols and Fatfy-ACII Sodium Salts in Jojoba-Wax Aqueous Hydrolyzate, article, 3 pages.
Hans Hoydonckx Dirk De Vos Suhas Chavan and Pierre Jacobs. Esterification and transesterification of renewable chemicals, . article, 2004, pp. 83-96, Belgium.
Busson-Breysse Farines and Soullert, Jojoba Wax its Esters and Some of its Minor Components. , 1994, pp. 999-1002, France.
Richard Hamilton and Yaquob Raie, Structure of the Alcohols Derived From Wax Esters in Jojoba Oil, article, 1974, pp. 92-96, England.
Shailesh Shah, Brajendra Sharma, Preparation and Evaluation of Jojoba Oil Methyl Esters as Biodiesel and as A Blend Component in Ultra-Low Sulfur Diesel Fuel, article, 2009, 10 pages.
Stethke, Weltkamp, Klein and Mukherjee, High-Yield Preparation of Wax Esters via Lipase-Catalyzed Esterification Using Fatty Acids and Alcohols from Crambe and Camelina Oils, article, 2001, pp. 647-651, Germany.
Michael A. Jackson, Isolation of long-chain aliphatic alcohols from beeswax using lipase-catalyzed methanolysis in supercritical carbon dioxide, article, 2006, pp. 173-177, USA.
McKinney and Jamison, A Non-Fatty Oil from Jojoba Seed, article, Oct. 1938, pp. 289-295, USA.
Thomas K. Miwa, Jojoba Oil Wax Esters and Derived Fatty Acids and Acohols Gas Chromatographic Analyses, article, Jun. 1977, pp. 259-264, vol. 48, USA.
Spencer, Plattner, and Miwa, Jojoba Oil Analysis by High Pressure Liquid Chromatography and Gas Chromatography/Mass Spectrometry, article, 1978, pp. 187-189, vol. 54 No. 5, USA.
Karande, Jain, and Mitragotri, Insights into synergistic interactions in binary mixtures of chemical permeation enhancers for transdermal drug delivery, article, 2006, pp. 85-93, Journal of Controlled Releasse 115, USA.
Karande, Jain, Ergun, Kispersky and Mitragotri, Design principles of chemical penetration enhancers for transdermal drug delivery, article, 2005, pp. 4689-4693, vol. 102 No. 13, USA.
Kanikkannan Kandimalla Lamba S.S Singh M.. Structure—activity Relationship of Chemical Penetration Enhan-cers in TransdermalDrug Delivery, article, 2002, 2 pages, vol. 7 No. 6.
Nanayakkara, Bartlett, Forbes, Marriott, Whitfield and Brown, The effect of unsaturated fatty acids in benzyl alcohol on the percutaneous permeation of three model penetrants, article, 2005, pp. 129-131, UK.
Franklin B. Wells, Jojoba Oil Liquid Wax and Some of its Applications, article, pp. 253-254, USA.
Molaison, O'Connor and Spadaro, Long-Chain Unsaturated Alcohols from Jojoba Oil by Sodium Reduction, article, pp. 379-382, USA.
Wisniak and Zabicky, Proceedings of the Sixth International Conference on Jojoba and its Uses, article, 1985, 7 pages, Israel.
Office of Arid Lands Studies, Jojoba A Wax-Producing Shrub of the Sonoran Desert, article, 1974. pp. 19-21, USA.
Memoria Proceedings, ra Basic and Applied Research on Jojoba, article, 1980, 12 pages, Mexico.
Brown, Arquette, and Reinhardt, Proceeding of 9th International Conference on Jojoba and its Use: topic Jojoba Esters, a new family of cosmetic emollients, article, 1966, pp. 99-103, USA.
Thomas K. Miwa, JoJoBa, Fundamental and Applied Research, Communications, Notes, Reviews, article, 1980, 41 pages, vol. 1, USA.

Williams and Barr, Enhancement in Drug Delivery, article, 2007, pp. 232-254, USA.
Walters and Hadgraft, Pharmaceutical Skin Penetration Enhancement, article, 1993, 3 pages, Wales.
Birgitte Mollgaard, Synergistic Effects in Percutaneous Ehnancement, article, pp. 229-426, Denmark.
E. Scott Pattison, Fatty Acids and Their Industrial Applications, article, 1968, pp. 220-232, USA.
Media release by Desert Whale Jojoba Company, 2006, 1 page, USA.
Brochure, New Jojoba Illuminate, 2009, 8 pages, USA.
Lin Lu Healy, Gelled Emollient Systems for Controlled Fragrance Release and Enhanced Product Performance, article, 2002, pp. 47-54, vol. 117 No. 2m, USA.
Research paper, Issues with enzyme and non-enzyme proteins contained in cosmetic ingredients.
Oct./Dec. International Federation Societies of Cosmetic Chemists Magazine, articles, 2009, 78 pages, USA.
A.R. Baldwin Seventh International Conference on Jojoba and its uses, book, 1988, 242 pages, USA.
Rheins, Harper, Sondgeruth, Ashley, Oliphara, Marshall, The Role of Hydrolyzed Jojoba Esters as a Unique Botanical Technology for Long-Acting Moisturization, Information Sheet, 1 page USA.
Ashley, Oliphant, and Harper, Retention of Sunscreen Actives is Improved in Formulas Containing Hydrolyzed Jojoba Esters as Measured by ATR-FTIR, information sheet, 4 pages USA.
Gilmore, Oliphant, and Harper, Beneficial Effects of Incorporating Hydrolyzed Jojoba Esters into Skin Care products, information sheet, 1 page, USA.
Gilmore, Oliphant, and Harper, Beneficial Effects of Incorporating Hydrolyzed Jojoba Esters into Skin Care Products—Presentation by T. Oliphant in NYC, information sheet, Dec. 10 to Dec. 11, 2009, 1 page USA.
Oliphant, and Ashely, FloraTech—Reduced Hair Damage withthe use of Hydrolyzed Jojoba Esters in a hair conditioner formula, information sheet, 1 page, USA.
Oliphant, and Ashley,FloraTech—Reduced Hair Damage with the use of Hydrolyzed Jojoba Esters in a Hair conditioner formula—Presentation by T. Oliphant in NYC, information sheet, Nov. 1 to Nov. 3, 2009, 1 page USA.
FloraTech—Pearlized Conditioning Shampoo with Floraesters k-29W Jojoba, information sheet, 2004, 1 page USA.
FloraTech—Technical Report—Cold process moisture elements body wash (body wash with Floraesters k-100 Jojoba (k-100), information sheet, 2009, pp. 1-9, USA.
Report for Evaluation of Moisturization and Skin Smoothing Effects of Jojoba Oils, report, Dec. 2, 1998, pp. 1-26, vol. 1, USA.
Report of the Effects of Jojoba Derivatives on Skin Moisturization and Barrier Function and Evaluation of Their Substantivity, report, Jan. 26, 1999, pp. 1-18, USA.
Report for Repeated Insult Patch Test (Modified Draize Procedure) Project No. 97-4246-74ABC, report, Jan. 6, 1998, pp. 1-7, USA.
Standards for Natural and Organic Cosmetics, book, 2003, 41 pages, Jourdain.
Demetrios M. Yermanos, Proceedings—3rd International Conference on Jojoba, article, Sep. 13, 1978, 6 pages, USA.
Revised Report for Evaluation of the Effects of Jojoba Oils on Skin Moisturization and Barrier Function and Evaluation of Jojoba Oil's Substantivity, report, Oct. 26, 1998, 90 pages, USA.
Evaluation of the Effects of Jojoba Derivatives on Skin Moisturization and Barrier Function and Evaluation of Their Substantivity, report, Jan. 26, 1999, 130 pages, USA.
Over-view of Soapmaking, htp//www.drbmner.com/soapmaidngoverview.html, website, 2002-2009, 1 page.
Definition of Jojoba Alcohol, Wikipedia, http//en.wildpcdia.org/wlki1Jojoba alcohol, website, Feb. 7, 2011, 1 page.
Jojoba Happenings, article, Jan.-Feb. 1989, pp. 1-8, vol. 17 No. 1 (78), USA.
Jojoba Happenings, article, Mar.-Apr. 1985, pp. 1-5, vol. 13 No. 3 (56), USA.

* cited by examiner

HIGH UNSAPONIFIABLES AND METHODS OF USING THE SAME

CROSS-REFERENCE TO RELATED PATENT APPLICATIONS

This patent application is a continuation of U.S. patent application Ser. No. 12/203,004, filed on Sep. 2, 2008, now U.S. Pat. No 7,955,611, which is a Continuation-In-Part of U.S. patent application Ser. No. 10/611,775, filed on Jun. 30, 2003, and is a Continuation-In-Part of U.S. patent application Ser. No. 09/478,071, filed Jan. 3, 2000, now U.S. Pat. No. 7,435,424, the contents of each of which is incorporated herein in its entirety by reference.

FIELD OF THE INVENTION

The present invention relates to a novel composition of matter derived from natural materials or extracts of natural materials. In particular the invention relates to substantive carriers derived from natural waxes, oils, and extracts, and in particular to substantive carriers derived from natural ingredients with relatively high levels of unsaponifiable materials (as defined below) and methods of using the same.

BACKGROUND

Vegetable and animal fats are organic lipid materials that generally contain esters of long-chain fatty acids and glycerine. Under certain conditions these esters react with water (hydrolysis) to form an alcohol (glycerine) and fatty acids. (Hydrolysis is the splitting of a compound into components by the addition of water and an enzyme, acid or base.) The results of a hydrolysis reaction are known as "hydrolysates". When heated in the presence of an alkali hydroxide, the above-mentioned esters yield soaps (alkali salts of the corresponding fatty acid) and glycerine; this particular hydrolysis process is called saponification. "Saponification" and "saponifying" are used herein in their normal manner to mean the hydrolysis reaction between a wax, oil or fat with an alkali metal or alkaline earth metal hydroxide to form the corresponding metallic salt soap. These fats and oils have a saponification value that is the number of milligrams of potassium hydroxide required for complete saponification of one gram of free organic acid and/or organic acid ester.

The post-saponification products may either be hydrophilic (water soluble) or hydrophobic (water insoluble). Herein, we will use the term "unsaponifiable" to mean those materials that, after the saponification reaction is completed, remain water insoluble. This is in full accordance with A.O.C.S. Official Method Ca 6b-53, which defines unsaponifiable materials as those substances frequently found as components of fats and oils, which cannot be saponified by the usual caustic treatment, but that are soluble in ordinary fats and oils. Included in, but not limited to, the group of unsaponafiable materials are higher aliphatic alcohols, sterols, pigments, mineral oils, and hydrocarbons. Unsaponifiable materials are generally non-volatile at 103° C. The weight percent of unsaponifiable material in a substance may be measured directly by measuring the weight percent of those materials defined as unsaponifiable.

Most well-known vegetable and animal lipids have low levels, less than 5 weight percent (<5%), of unsaponifiable materials. This means that most of the products of the saponification reaction are water-soluble. Commonly used vegetable oils have levels of unsaponifiable materials generally below 1 weight percent. For example, saponification of soybean oil leaves 0.7 weight percent unsaponifiable materials, saponification of olive oil leaves 1.2 weight percent unsaponifiable materials, and saponification of peanut oil leaves 0.4 weight percent unsaponifiable materials. However, some commercial oils contain higher concentrations of unsaponifiable products, up to as much as 6.0 weight percent unsaponifiable materials. Examples include: crude rice bran oil, 4.2 weight percent unsaponifiables; crude wheat germ oil, 6 weight percent unsaponifiables; and shea butter, 9-to 13 weight percent unsaponifiables. Materials with high levels of unsaponifiables, such as shea butter, are not a preferred starting material for the production of soap because of the relatively high amount of unsaponifiable materials left after the saponification reaction.

In most cases, the hydrolysis products of a saponification process are used for a single purpose—as hygienic skin-cleansing agents (i.e., soaps). In the past, the basic ingredient of soap was animal fat (also known as lard or tallow) with wood ash-based lye used in the saponification process. Ideally, a bar of soap has a suitable hardness to maximize user cycles and has a certain amount of resistance to water reabsorption when not in use, while at the same time providing sufficient lather (i.e., acting as a foaming agent) to enhance the cleaning ability of the soap. Animal lipids as the active ingredient in the soap making process will generally meet these user demands to a greater or lesser degree. Current soap production continues to rely heavily on animal fats in their production to meet consumer demand and manufacturing requirements, although more and different types of synthetic materials have found use in modern soap compositions. Various synthetic compounds and mixtures of compounds have become popular additions in soap making technology for their improvement of soap quality and user satisfaction. However, these synthetic-based soaps are generally resistant to the natural breakdown processes (i.e., biodegradability) and are thus relatively persistent in the environment.

There are basically two distinct types of soap manufacturing processes. In a first method, oils and fats are boiled in an open kettle with caustic alkali solutions, bringing about saponification gradually until all of the fats and oils are completely saponified, followed by the removal of glycerine. This process may either run in batch or in a continuous process.

In a second method, which is typically a continuous method (but may be run in batch form), fatty acids and alkali are brought together in proper portions for complete saponification in a mixing valve or other device which brings them into intimate contact. The progress of saponification depends on the temperature, time of contact and efficiency of mixing. Concentrated solutions produced by these methods are referred to as "neat" soaps, and possess a concentration of 60-65% soap, about 35% water and traces of salt and glycerine. It is from this product that consumer soaps in the form of bars, flakes, granules and powders are produced; by first drying the neat soap into pellets having a moisture content of about 12-16% followed by finishing steps, such as milling, plodding, amalgamating, and the like.

Consumer bar soaps today are manufactured from coconut oil and/or tallow or their fatty acids. Palm kernel oil is sometimes substituted for coconut oil for economic reasons, and soaps prepared with palm kernel oil are adjusted for performance characteristics similar to non-substituted tallow/coconut formulations. Palm oil is also often substituted for tallow.

A consideration in selecting materials for making soap is the proper ratio of saturated versus unsaturated, and long-versus-short-chain fatty acids that result in a soap having the desired qualities of stability, solubility, ease of lathering, hardness, cleaning ability, and the like. It has been determined that soaps prepared from fatty acid mixtures wherein a majority of the fatty acids in the mixtures have carbon chains less than twelve atoms irritate skin. Soaps prepared from saturated $C_{16}$ and $C_{18}$ fatty acids are typically too insoluble for consumer use. Thus, the preferred materials for soap production have fatty acid chains between twelve and eighteen carbon atoms in length.

Saponification of tallow produces a soap comprised of a mixture of fatty acids of $C_{14:0}$, $C_{16:0}$, $C_{18:0}$, and $C_{18:1}$ (myristic, palmitic, stearic and oleic acids, respectively) and saponification of coconut oil produces a soap comprised of a mixture of fatty acids of $C_{12:0}$ and $C_{14:0}$ (lauric acid and myristic acid, respectively) and significant amounts of $C_{8:0}$ and $C_{10:0}$ fatty acids. Consumer soap preparations usually contain tallow/ coconut (T/C) ratio ranges from approximately 90:10 to 75:25. Since lauric acid is found only in the coconut fraction of T/C mixtures, the most dramatic change observed in increasing the percent of the coconut fraction of T/C mixtures is the increase in lauric acid. Increasing the coconut fraction in T/C fatty acid containing soaps generally improves the desirable foaming characteristics of such soaps. However, in soaps with T/C ratios of 50:50, the desirable skin mildness properties are reduced.

Typical fatty acid distribution (in weight percent) of the main soap making components is given below:

| Carbon Chain Length | Tallow | Palm | Coconut | Palm Kernel |
| --- | --- | --- | --- | --- |
| 10:0 (capric)    | 0.1  | 0.0  | 15.1 | 6.4  |
| 12:0 (lauric)    | 0.1  | 0.3  | 48.0 | 46.7 |
| 14:0 (myristic)  | 2.8  | 1.3  | 17.5 | 16.2 |
| 16:0 (palmitic)  | 24.9 | 47.0 | 9.0  | 8.6  |
| 18:0 (stearic)   | 20.4 | 4.5  | 9.0  | 8.6  |
| 18:1 (oleic)     | 43.6 | 36.1 | 5.7  | 16.1 |
| 18:2 (linoleic)  | 4.7  | 9.9  | 2.6  | 2.9  |
| 18:3 (linolenic) | 1.4  | 0.2  | 0.0  | 0.0  |
| 20:0 (arachidic) | 1.8  | 0.3  | 0.0  | 0.4  |

From the table it can be seen that the coconut and palm kernel fats (both known as lauric fats) are particularly rich in the $C_{10-14}$ saturated fatty acids, particularly derivatives from lauric acid itself. Another fat that contains saturated, relatively short chain fatty acids similar to coconut oil is babassu oil. In contrast, tallow and palm oil per se are industrial sources of non-lauric fats, especially those containing $C_{16}$ and $C_{18}$ fatty acids.

In general the longer chain fatty acid alkali salts, particularly the less expensive $C_{16}$ and $C_{18}$ salts (as obtained from tallow and palm oils), provide structure in the finished soap bars and prevent or retard disintegration of the soap bar on exposure to water. The more expensive, shorter chain, lauric fat-derived, (i.e., lauric acid salts) and other soluble salts (typically as obtained from coconut and palm kernel oil) contribute to the lathering properties of the overall composition. A general problem in the formulation of bar soaps has been finding a balance between providing structure (generally obtained from the long chain component) and maintaining lathering properties (generally obtained from the more expensive short chain component) at a practical overall cost.

In addition to fatty acid salts, soap bars can contain free fatty acids. The addition of free fatty acids is known as "superfatting". Superfatting at a 5-10% free fatty acids level is known to give a copious, creamy lather. Other superfatting agents used include citric and other acids that function by promoting the formation of free fatty acids in the fat blend.

For the manufacture of the soap cakes, common additives can be added to the base soap in conventional quantities, such as overgreasing agents (1 to 3 weight percent), stabilizers (antioxidants, complexing agents) (0.05 to 0.5 weight percent), perfume (0.5 to 3 weight percent) and possibly dyes (0.05 to 0.3 weight percent) as well as skin protection agents such as sorbitol, glycerine or the like (1 to 5 weight percent).

The pharmaceutical and cosmetic industries have been using fat extracts of vegetable origin since earliest times. A number of years ago it became apparent in these industries that particularly valuable biological properties resulted from the use of vegetable fats or extracts of vegetable fats rich in unsaponifiable materials. Certain vegetable oils, for example avocado, and, in particular, shea butter, are known to be particularly rich in unsaponifiable materials and/or to contain, these unsaponifiable materials.

A process for enriching unsaponifiables in oils, especially shea butter, for use in cosmetic and pharmaceutical compositions is described in U.S. Pat. No. 5,679,393, issued to Laur. This process concentrates the unsaponifiable fraction of fats and oils by the processes of crystallization and fractionation. This method is expensive and it does not liberate the alcohol moiety from the starting compounds (hydrolysis). Thus, the Laur process and methods for use of the products thereof never utilize hydrolysis to create alkali salts and liberate alcohols and other unsaponifiables.

Hydrolysates applied topically to animate and inanimate objects find use in numerous non-cleansing areas ranging from cosmetic preparations, pharmaceuticals, hydration formulations, insecticides, insect repellant, and the like. One of the areas of interest created by the varied uses of topically applied agents is maximizing the duration a topically applied active agent is present on the applied surface (substantivity). As a result of this intense interest, the search for ways to improve the duration of a fixed amount of topically applied cosmetics, pharmaceuticals, and bioactive agents has been of prime importance in all areas wherein topically applied cosmetics, pharmaceuticals, and bioactive agents are employed. An example of this interest may be found in the prior art relating to sunscreen compositions.

The use of sunscreen compositions is required by a large segment of society since many of those exposed to sunlight do not have the natural pigmentation which provides protection against the harmful effects of solar radiation. Because many people show erythema under even short exposures to sunlight, there is a need for sunscreen compositions that protect against erythema-causing radiation (i.e., ultraviolet radiation) so that longer exposure to sunlight with less risk of sunburn is possible.

A variety of sunscreen compositions are known in the art. One tendency in formulating sunscreen compositions has been to prepare compositions that are water-resistant to the skin. One method is to chemically modify the ultraviolet absorber to increase its interaction with the skin using quaternizing imidazoles, as described in U.S. Pat. No. 3,506,758; another method is to copolymerize ultraviolet light absorbing monomers with other monomers to form water-resistant films, as described in U.S. Pat. Nos. 3,529,055 and 3,864,473; yet another method is to form polymeric films with water-insoluble polymers, as described in U.S. Pat. No. 3,784,488.

The use of the acid form of crosslinked ethylene-maleic anhydride copolymers to retain ultraviolet light absorbers is disclosed in U.S. Pat. No. 3,821,363. The use of water insoluble acrylate polymer is disclosed in U.S. Pat. No. 4,172, 122. The use of water-insoluble, alcohol-soluble, film-forming poly-amide materials is disclosed in U.S. Pat. No. 3,895,104 solely for the purpose of providing improved substantivity.

Cosmetic and other applications of the prior art have not heretofore utilized the substantivity inherent in hydrolysates of naturally derived materials containing high unsaponifiables or long chain esters (greater than 18 carbons in length) to enhance the intrinsic substantivity of topically applied agents with which they are incorporated. The purpose of employing polymers or polymeric materials in the compositions of the prior art has been directed towards improving the adherency (i.e., substantivity) of the topical material to the skin or have been employed solely as thickening agents. The improved substantivity, among other properties, achieved by employing the hydrolysates according to the present invention has not heretofore been disclosed or appreciated in the prior art.

The increased substantivity of topically applied agents provides for more effective and economical use of such materials. In particular, the present invention provides improved compositions, including emollients, skin hydrating agents, sunscreens, lipsticks, makeup, insect repellants, insecticides, pesticides, herbicides, and the like, having at least an effective amount of a hydrolysate including high levels of unsaponifiable materials, preferably of long chain alcohols.

SUMMARY OF THE INVENTION

The hydrolysis of materials with high levels of unsaponifiable matter, such as extracts from plants, result in products with unique properties. Conventional products of saponification of natural oils function as they do as a result of the low level of unsaponifiable materials contained therein (as discussed above). Such properties include high levels of aqueous surfactant activity, water-solubility and/or ready water-dispersability, activity as foaming agents, and the like. The very objective of traditional saponification processes is to increase the water-solubility and surfactant activity of naturally occurring materials. It has been found that the application of hydrolysis to materials, particularly naturally derived materials, with a high unsaponifiables fraction (e.g., at least 6 weight percent of the material) in combination with a saponifiable fraction produces a hydrolysate with properties that are significantly different from those products resulting from conventional saponification of materials with less than 6 weight percent of unsaponifiables.

The resulting products from the practice of the present invention are substantive, water resistant, prevent unwanted absorption of a carried active ingredient by the applied surface, exhibit a unique surfactant functionality, and are not foaming agents with water. Some unexpected uses for the resulting hydrolysates have been found to be as an emollient and/or an alternative natural carrying agent for topical application of cosmetics, pharmaceuticals, and bioactive agents, particularly to the skin of subjects, and provide a substantive support for the materials carried.

The novel features that are considered characteristic of the invention are set forth with particularity in the appended claims. The invention itself, however, both as to its structure and its operation together with the additional object and advantages thereof, will best be understood from the following description of the preferred embodiments of the present invention when read in conjunction with the accompanying drawings. Unless specifically noted, it is intended that the words and phrases in the specification and claims be given the ordinary and accustomed meaning as understood by those of ordinary skill in the applicable art or arts. If any other meaning is intended, the specification will specifically state that a special meaning is being applied to a word or phrase. It is intended that the present invention not be limited only to the specific structure, material or acts that are described in the representative embodiments, but in addition, include any and all structures, materials or acts that perform the claimed function, along with any and all known or later-developed equivalent structures, materials or acts for performing the claimed function.

DETAILED DESCRIPTION OF THE INVENTION

The present invention is a composition of matter, and method for using the same, which is useful as a topically applied material with several useful inherent properties, such as substantivity. Additionally, the composition is useful for carrying an effective amount of topically applied active materials. More specifically, the composition according the present invention provides a carrying agent for the topical application of materials when superior "lasting" power or substantivity is required. Additionally, the present invention is useful because, among other things, it acts as both an emollient and emulsifier and demonstrates substantivity—that is to say, it has the ability to "fix" many different types of "active" materials, from sunscreens to pharmaceutical preparations, to any applied animate or inanimate surface.

For the purposes of this invention, the following definitions should be considered:

"High unsaponifiable materials" or "high unsaponifiable content" oils, waxes, fats, and the like, means compositions that comprises at least 6 weight percent of total organic materials that are unsaponifiable and at least 10 weight percent of organic materials that are saponifiable (N.B., it is possible that the percentage of unsaponifiables may even exceed 95 weight percent in some formulations). Therefore, the term includes compositions containing from 6-90 weight percent of organics of unsaponifiable materials and 10-94 weight percent of saponifiable materials. Examples of bio-based materials with high unsaponifiables are listed in the table below.

| Material | % Unsaponifiables |
|---|---|
| amaranth seed oil | 9% |
| anise seed oil | 7% |

-continued

| Material | % Unsaponifiables |
| --- | --- |
| avocado seed oil | 57% |
| barley oil | 6% |
| briza oil | 78% |
| buck wheat oil | 7% |
| candelilla wax | 65-75% |
| carnuba wax | 50-55% |
| Cassia occidentalis oil (wild coffee) | 7% |
| coffee bean oil | 8% |
| deoiled lecithin | 32% (in Theory) |
| dog fish oil | 16-18% |
| esparto wax | 42-49% |
| oils from fungi and other microorganisms | 6% or greater |
| guayule (plant material extract) | 8-12% |
| jojoba oil | 45% |
| jurinea oil | 40% |
| lanolin | 39% |
| laurel berry oil | 6% |
| olestra(TM) or olean(TM) | 33% (approximation) |
| olive oil concentrate (phytosqualene) | 35-75% |
| olive seed oil | greater than 6% |
| orange roughy oil | 40% |
| ouricury wax | 50-55% |
| quinoa seed oil | 6% |
| rye germ oil | 11% |
| sharkliveroil | 60% |
| shea butter | 9-13% |
| sperm whale oil | 36% |
| sugar cane wax | 18-80% |
| sunflower wax | 25-45% |
| tall oil | 9-23% |
| tall oil distillate | 25-33% |
| Vegepure(TM) from wheat grains | 70-90% |
| wheat germ oil | 6% |

"Substantivity" means the tendency of a material to resist being easily removed or the persistence of a treatment on the skin. For example, some sunscreen lotions are substantive because they form a film on the skin that is relatively water-insoluble. This, then, means that substantive materials resist removal or transfer by physical contact, sweating or washing.

Compositions of matter comprising waxes, oils and/or fats (lipids) containing at least 6 weight percent unsaponifiable ingredients and at least 10 weight percent saponifiable ingredients are subjected to an alkaline hydrolysis reaction to produce a non-foaming, substantive composition with unique surfactant properties that may be used as an active ingredient or as a carrier for application of other active ingredients, e.g., as a carrier base for application of cosmetic, pharmaceutical or other active ingredients. Commercially available bio-based extracts that have high unsaponifiables include, but are not limited to, candelilla wax, carnauba wax, jojoba oil, lanolin, lecithin, and shea butter.

The lipid that is subjected to the process of the present invention may be a raw product or can also undergo various refining and/or modification steps beforehand. Examples of refining processes which may be mentioned are the conventional processes of chemical or physical refining or the more specialized processes for the refining of shea butter, which make it possible in particular to retain or concentrate the maximum amount of unsaponifiable materials, thereafter subjecting such treated materials to the process of the present invention.

The chemical refining which is preferentially used, being applied to the vegetable fats before they are subjected to the process according to the present invention, may be any conventional chemical refining process, in particular any process comprising the following steps:

Step 1: degumming involving insolubilization of the phosphatides with water, generally in the presence of acid, most frequently phosphoric acid, and separation by decantation or centrifugation;

Step 2: neutralization of the free fatty acids in the oil by the addition of a sodium hydroxide solution and separation of the soaps formed (called soap stock), most frequently by centrifugation followed by several washes with water, often being performed simultaneously with degumming in a continuous process;

Step 3: decolorization with activated bleaching clays at about 100° C. under reduced vacuum, and filtration;

Step 4: deodorization to remove compounds responsible for the odors and flavors of an oil and for producing refined oil. This operation is carried out in an apparatus called a deodorizer—the procedure involving heating of the oil to a high temperature (180°-220° C.) under vacuum on the order of 4 Torr (about 532 Pa) with the injection of steam to strip away impurities.

An alternative physical refining method involves a variant of the chemical refining process explained above, the difference being that the neutralization step with sodium hydroxide is not performed and the removal of the free fatty acids from the oil is effected during the deodorizing step. The refinement conditions selected during this physical refining method may require suitable modification in order to retain the desired properties of the high unsaponifiables selected for use during the procedure for preparation of the present invention.

The extracts used as starting materials for the hydrolysis reaction according to the method of the present invention may be in their raw or refined states. The extracts may also be alkoxylated, polymerized, acetylated, oxidized, reduced, concentrated, hydrogenated, partially hydrogenated, interesterified, double bond modified, randomized, refined, or otherwise modified before the hydrolysis reaction. Since many lipids have low concentrations or fractions (for example 1 weight percent or less as discussed above) of unsaponifiables, the present invention encompasses the concentration of low fraction unsaponifiables into higher fractions, i.e., greater than 6 weight percent.

Products from the hydrolysis reaction of organic materials that produce unsaponifiables comprises a mixture of polar hydrophilic salts (saponifiables) and non-polar, lipophilic materials (unsaponifiables), with the possibility of other materials also present, depending on the source, state and form of the initial reactant.

The composition of materials created by the method according to the present invention are produced by the reaction of aqueous alkali metal or alkali earth metal hydroxides, e.g., NaOH, LiOH, KOH (a preferred hydroxide), $Ca(OH)_2$, $Mg(OH)_2$, and/or the like, with organic lipid compositions, usually plant extracts, oils, fats, or waxes (of the extracts or derivatives of the extracts) where the organic compositions contain a high proportion of unsaponifiable materials (greater than 6 weight percent), and preferably as long chain esters.

Jojoba oil may be examined as an exemplary case. Refined jojoba oil contains various proportions of long chain di-unsaturated esters. Hydrolysates of refined jojoba oil are nearly a 55:45 mixture of polar hydrophilic long chain salts (alkali salts) and relatively non-polar lipophilic materials (fatty alcohols). The lipophilic fraction is the unsaponifiable materials according to the definition used in this document. The carbon chain lengths of both jojoba hydrolysate fractions include and vary from $C_{18}$ to $C_{24}$ and have ω-9 double bonds as part of each molecule. It has been found that the combination of saponifiable and unsaponifiable fractions of the hydrolysates according to the present invention has properties that aid in the formulation of cosmetic, pharmaceutical, and other compositions.

The products that result from the hydrolysis of the lipids containing high percentages of unsaponifiable materials, as created during the practice of the present invention, whether used neat, blended, dissolved, dispersed, or emulsified with excipients, solvents, or carriers, can contain and impart useful properties to applied surfaces. These surfaces may be animate surfaces, particularly human skin, plant surfaces, and even the surfaces of inanimate objects, for example objects of wood, fiber, or plastic. The properties can include, but are not limited to, substantivity, emulsification, hydration, and/or the like.

One of the above-mentioned properties, substantivity, is particularly useful in the field of lipstick, shampoos, conditioners, hair sheens, repellants, attractants, cosmetics, pharmaceuticals, and sunscreens. The property of substantivity is especially beneficial to hair care products, such as "leave in" hair conditioners, where naturally derived materials that display substantivity are particularly commercially desirable. Substantivity is also particularly useful with sunscreen, sun block, or tanning formulations, as well as with insect repellants, such as tick, flea and fly repellants, and pesticides. Substantivity may also be beneficial when used on inanimate objects, such as with air fresheners, antibacterial, anti-mildew, and antifungal agents, flystrips, pesticides, insecticides, insect repellants, herbicides, and the like.

It is theorized that the inclusion of the high levels of unsaponifiable materials in the organic material enables the hydrolysates according to the present invention to display their unique combination of properties. The precise nature of the unsaponifiable materials within the oils, waxes, fats or other natural extracts is not particularly important (except when a specific property is desired), and each of the variously available natural starting materials may differ significantly in their composition and types of unsaponifiables. For example, Jurinea extracts (e.g., the petroleum ether extracts of Jurinea) may comprise 40 weight percent of pentacyclic triterpene alcohols together with their esters (myristate, palmitate, and acetate) as well as $\alpha$-amyrin, $\beta$-amyrin, lupeol, and taraxasterol such as t-taraxasterol (Lipids, K. L. Mikolajczak et al., 1967, Vol. 2, No. 2, pp. 127-132). Briza oil may contain 20 weight percent of lipids that are semi-solid, the lipid comprising 49 weight percent unsaponifiable digalactosylglycerides, 29 weight percent unsaponifiable monogalactosylglycerides and small amounts of conventional saponifiable triglycerides. The predominant fatty acids in the above oils are palmitic acid, oleic acid and linoleic acid (Lipids, C. R. Smith, Jr. et al., March 1966, Vol. 1, No. 2, pp. 123-127).

The composition according to the present invention is preferably produced in a batch process using a large steam kettle equipped with a propeller mixer.

A measured quantity of potassium hydroxide pellets is added into the steam kettle with a measured quantity of distilled, deionized, or reverse osmosis purified water. The amount of potassium hydroxide employed in order to completely saponify the free organic acid and/or organic acid ester can be calculated from the saponification value of the starting material and will, in theory, be the stoichiometric amount. In practice, however, it is preferred to employ slightly less than the stoichiometric amount of potassium hydroxide in order to ensure that the hydrolysates that are formed are not contaminated with unused alkali. The amount of potassium hydroxide employed may be considerably less than the stoichiometric amount, for example, as little as 50% of the stoichiometric amount or less may be used depending upon the desired result. It is to be understood, however, that an amount of potassium hydroxide in excess of the stoichiometric amount, for example, up to 10% more than the stoichiometric amount, may be employed if complete saponification of the organic acid or ester is to be achieved. Excess potassium hydroxide remaining at the end of the reaction may be removed by traditional methods.

The potassium hydroxide pellets and water are stirred together with the propeller mixer until the potassium hydroxide pellets are dissolved. It is important to note, for safety purposes, that heat is generated during this step and the mixture is quite caustic. Individuals nearby should wear gloves, eye and face protection, and clothing protection to avoid burns, both thermal and chemical.

Next, a measured quantity of a refined or derivatized organic material containing a high proportion of unsaponifiables, such as jojoba oil, is gently added to the steam kettle, taking care not to splash the caustic solution contained therein.

The steam kettle is heated to 90-95° C. and held at temperature under constant agitation for two hours. At this point, the resulting mixture should be pH tested. If the solution pH is greater than 10.0, continue heating the mixture under constant agitation at 90-95° C. Retest the solution periodically until the pH is 10.0 or less.

Once the pH is 10.0, or less, withdraw a sample for analysis. This sample should be analyzed by methods such as chromatography or by another like or similar method, to show that the reaction has proceeded as desired.

The resultant hydrolysate may then be diluted by adding a second measure quantity of water, or other diluent, to the steam kettle and stirred with the mixing propeller. Heat should be continuously applied, less than 80° C., until the mixture is homogeneous.

Once homogeneous, the hydrolysate mixture is cooled to 60° C. while continuing the mixing with the propeller. The hydrolysate mixture may then be transferred to a holding container and allowed to cool to room temperature before sealing the holding container.

Emulsification is the process of dispersing one material throughout another in separate droplets and effecting a dispersion that will retain its physical characteristics for a period of one to two years at least. The influence on emulsifier type selected for use is related to the ratio of hydrophilic and lipophilic character expressed by the emulsifier with reference to a similar, although reciprocal, character of the oil being emulsified. These two properties have been termed Hydrophilic-Lipophilic Balance (HLB) of the emulsifier and required HLB of the oil. The HLB system is helpful to the emulsion formulator for the purpose of matching the appropriate emulsifier to a given oil. This matching is usually done experimentally, however, when the HLB of an emulsifier and the HLB requirement of a given oil is known, this experimentation can be greatly reduced. The HLB of the present invention exhibits a unique property of being 3 to 4 HLB numbers wide and in the hydrophilic range. An emulsifier with a wide HLB effective range is advantageous due to the flexiblity offered by such an emulsifier. The wide HLB effective range of the present invention also provides formulations with an extra margin for dealing with unusual conditions such as pH, heat, cold, and the like, that may be encountered in the normal distribution of cosmetics, pharmaceutical and other bioactive products.

It was noted during an experiment that when a concentrated fly repellant (Purina®, Societe des Produits Nestle S.A. Horse Spray Concentrate Insecticide) was diluted according to instructions, the resulting mixture separated and required re-integration by shaking before use. This separation of components was eliminated by addition of the hydrolysates according to the present invention, thus demonstrating the unique emulsification property of the hydrolysates.

Below are described several representative exemplary uses found for the hydrolysates in accordance with the present invention.

EXAMPLE 1

Enhanced Skin Hydration

A Novameter (Nova Technology Corporation) is an impedance measuring device that is designed and commonly used to provide a non-invasive, objectively reproducible method of measurement for quantifying a biophysical character relative to hydration of the skin. Ten panelists participated in a skin hydration study that utilized a Novameter to register and record results. The test was conducted according to the following procedure.

Figure 1:
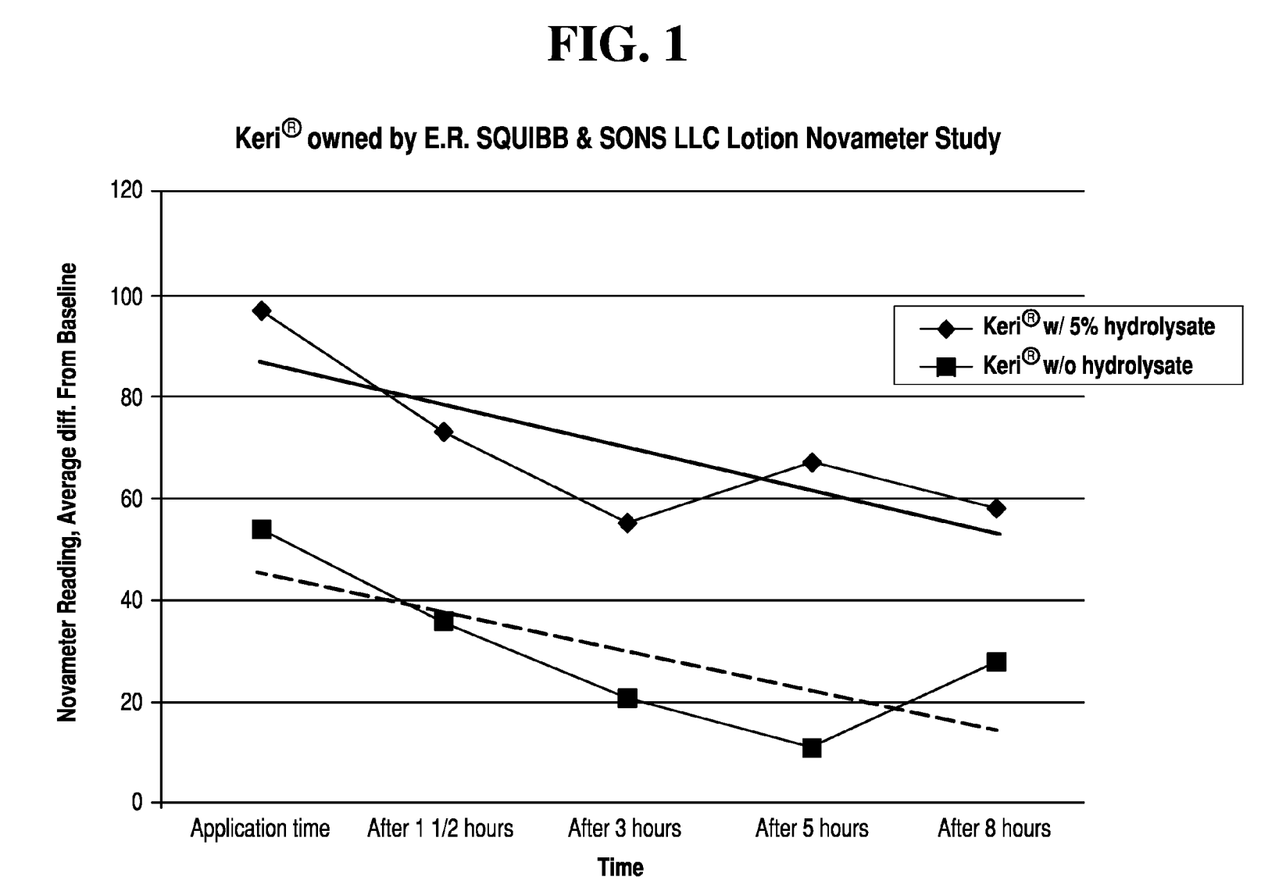
FIG. 1 is a graph of the effects of the hydrolysate when used with a hydrating lotion.

A commercially available skin lotion was purchased and divided equally. Half was used as a control and half was used as a base into which 5% of a jojoba hydrolysate was incorporated. The jojoba hydrolysate was prepared according to the method disclosed in this invention. A baseline skin hydration reading was taken with the Novameter for each panelist in advance of any lotion application. The control and hydrolysate containing lotions were applied to different areas of each panelist's forearms. The hydrolysate containing lotion was applied to the right forearm and the control lotion was applied to the left forearm. The Novameter was used to take skin hydration readings of the forearm areas to which each participant had applied each lotion. Multiple skin hydration readings were taken and recorded at two-hour intervals after lotion application. The results are illustrated in FIG. 1.

The experiment resulted in a dramatic increase in skin hydration for most all test subjects in the test areas where the hydrolysate formulation was applied, compared to the test areas of the control formulation. In general, 6 to 10 hours after application, the hydrolysate lotion formulation demonstrated a 20% to 54% improvement in skin hydration over baseline areas. The hydrolysate formulation showed a 10% to 47% improvement in skin hydration over skin treated with the control formulation.

EXAMPLE 2

Reduced Dehydration

Two makeup formulas were prepared: a hydrolysate formulation containing 5 weight percent of a hydrolysate according to the present invention and a control formulation containing an extra 5 weight percent water. The 5 weight percent water was added to the control formulation to keep the remaining ingredient compositions the same between the two formulations. The control formulation was applied on the left forearm and the hydrolysate formulation was applied on the right forearm.

Figure 2:
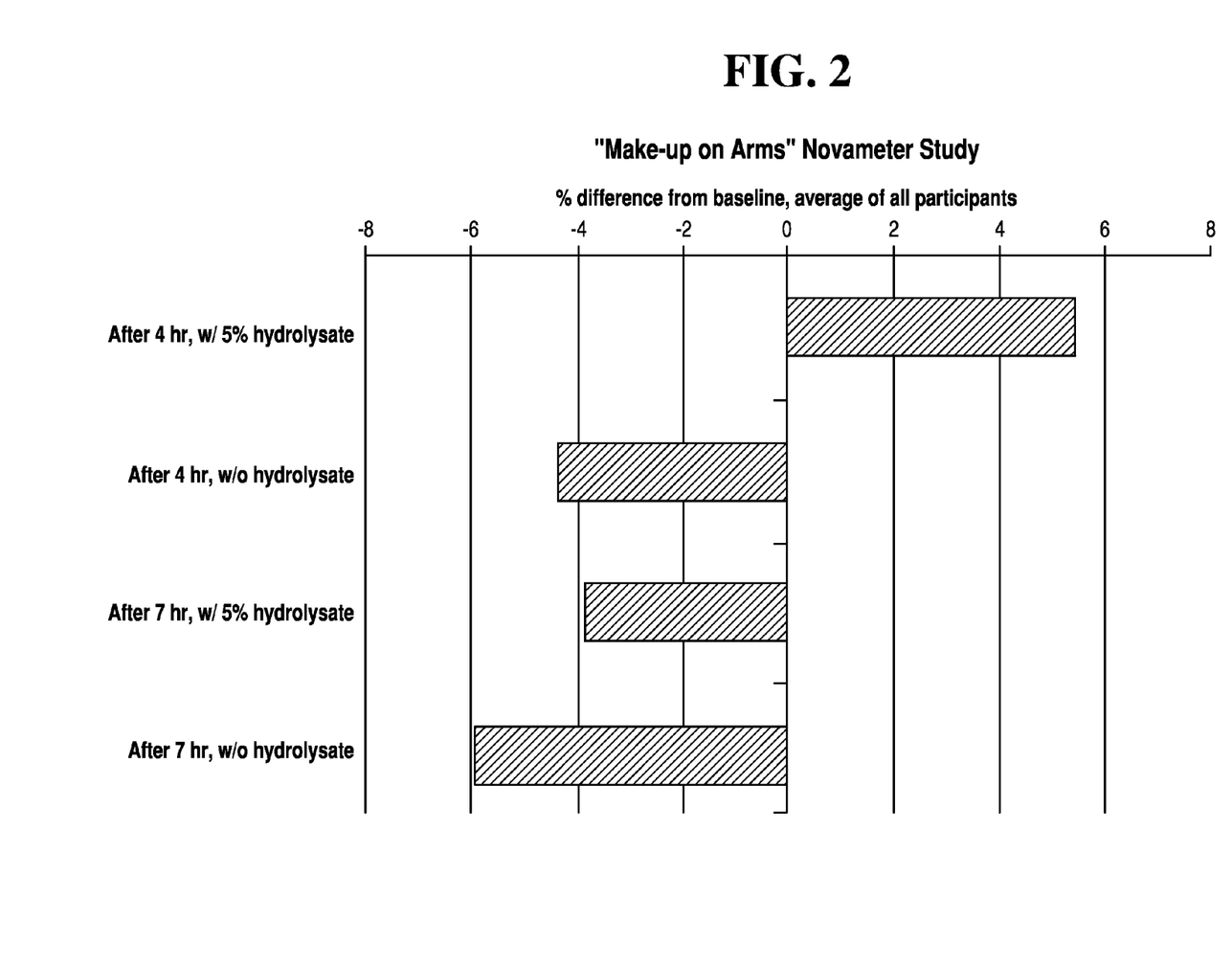
FIG. 2 is a graph of the effects of the hydrolysate when used with makeup.
Figure 3:
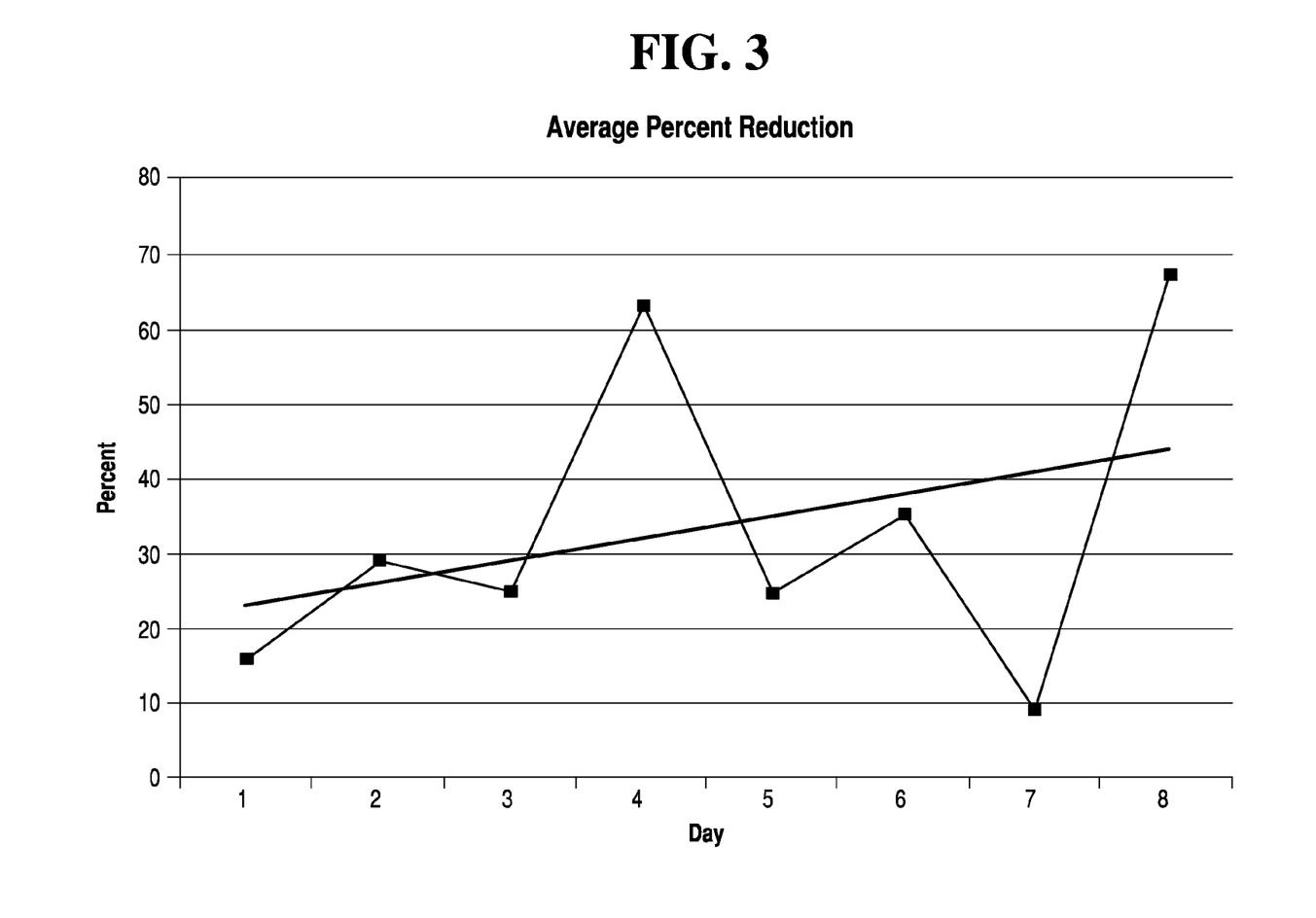
FIG. 3 is an illustration of the average percentage of fly reduction when fly spray incorporates the hydrolysates according to the present invention.
Figure 4:
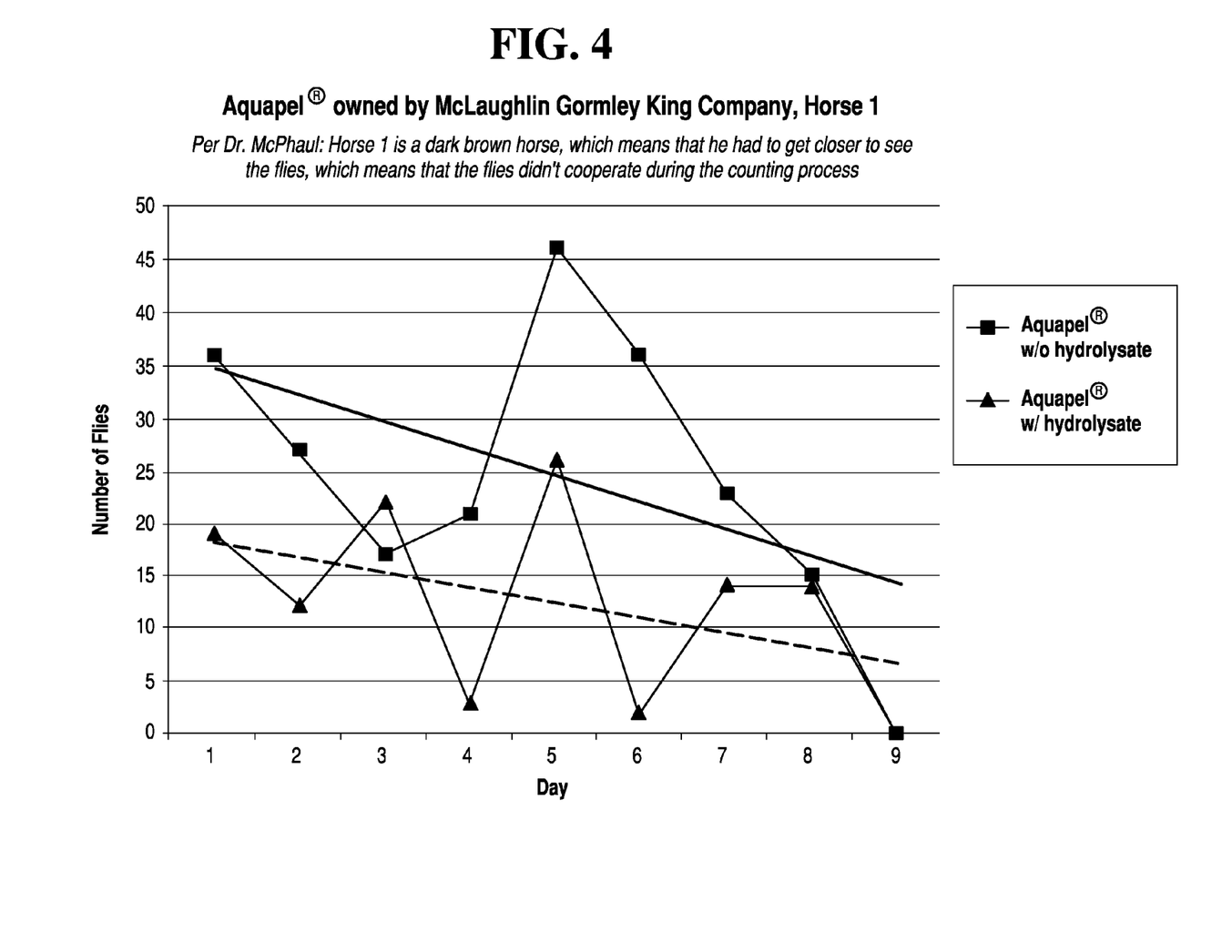
FIG. 4 is a graph of the fly reduction for Aquapel® (McLaughlin Gormley King Company) when incorporating the hydrolysates of the present invention.
Figure 5:
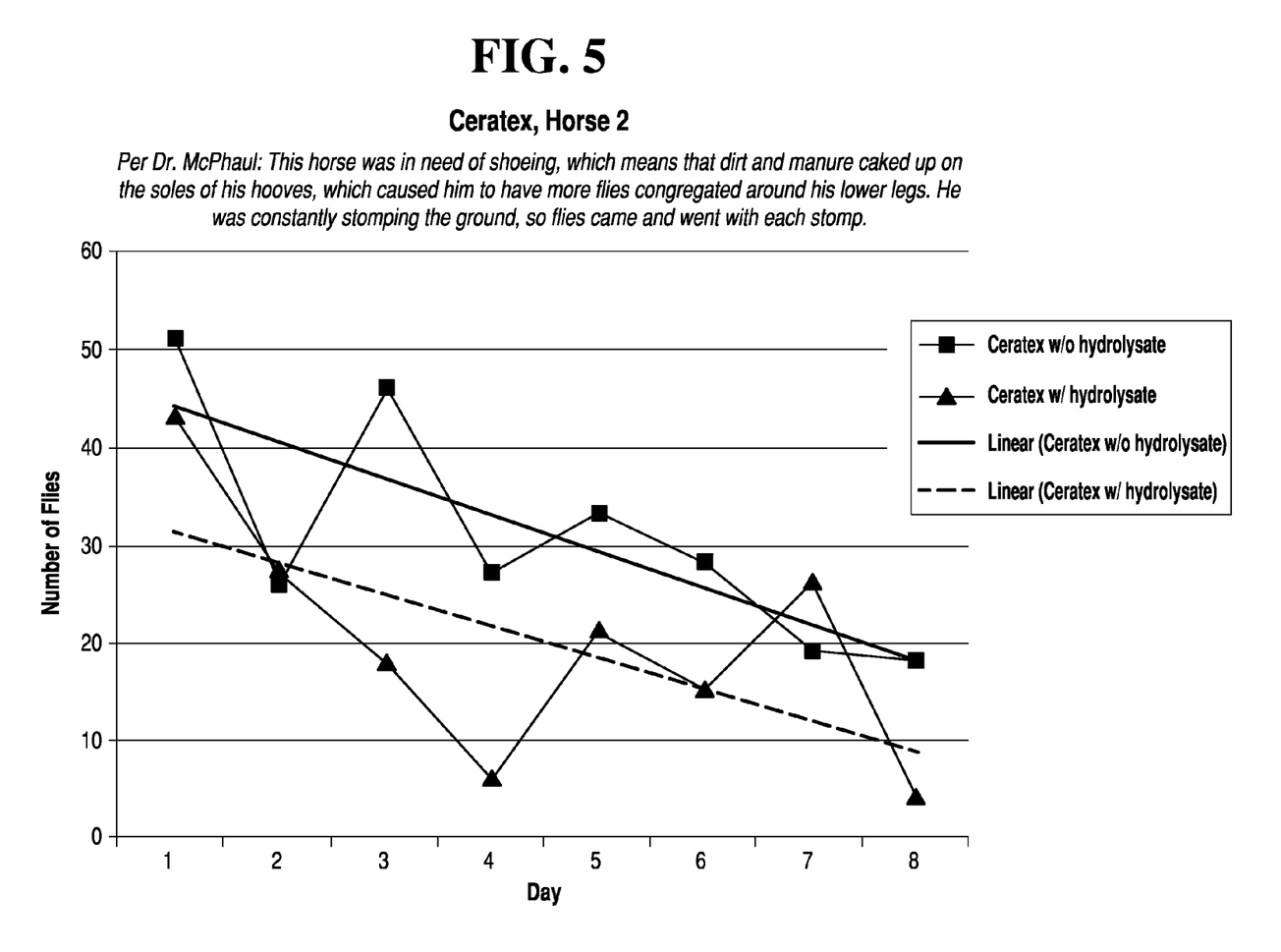
FIG. 5 is a graph of the fly reduction for Ceratex when incorporating the hydrolysates of the present invention.
Figure 6:
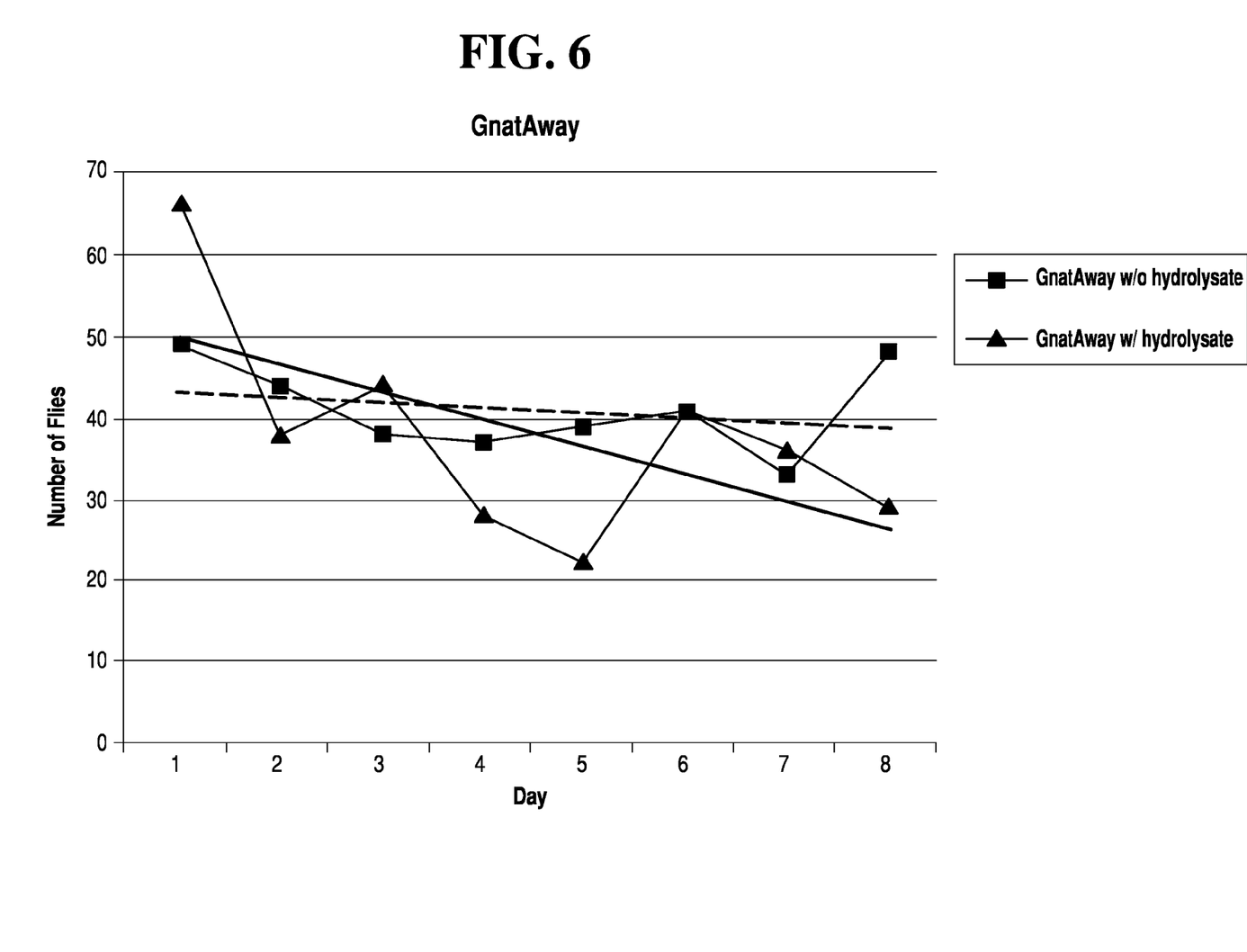
FIG. 6 is a graph of the fly reduction for GnatAway when incorporating the hydrolysates of the present invention.
Figure 7:
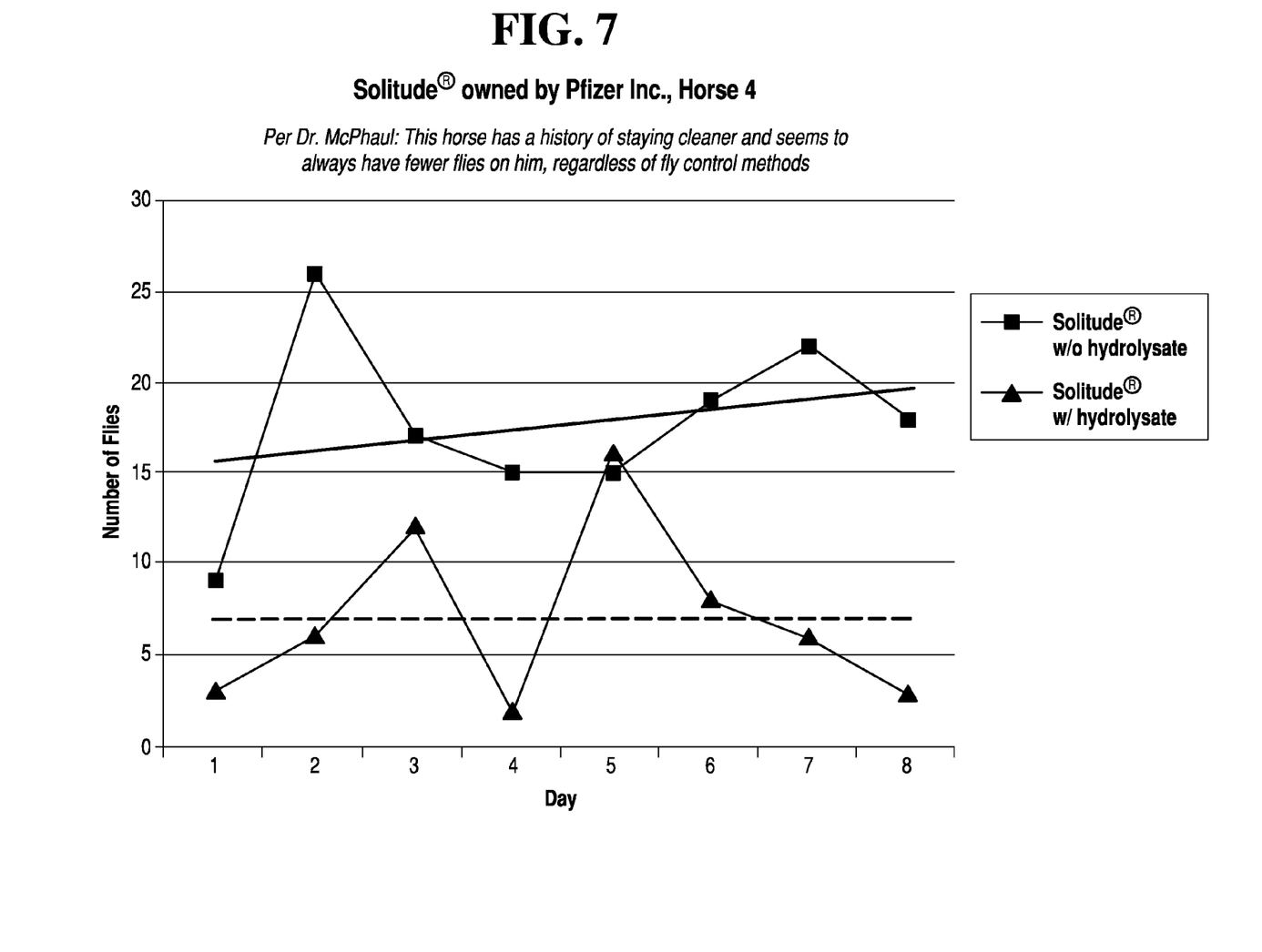
FIG. 7 is a graph of the fly reduction for Solitude® (Pfizer Inc.) when incorporating the hydrolysates of the present invention.

A Novameter was used to take baseline hydration readings of each participant before makeup application and to take hydration readings at intervals of four and seven hours after application of each formulation. The results were averaged for each person using the control and hydrolysate containing lotions to determine the percent difference in skin hydration from the baseline. The results are shown in FIG. 2.

At four hours after makeup application, the average Novameter readings of the participants showed an increase in skin hydration of approximately 5% over baseline on areas to which the hydrolysate formulation had been applied. A reduction in skin hydration of approximately 4% from baseline was observed on the areas with the control formulation. The difference between the hydrolysate and control formulations was approximately 9%, with the hydrolysate formulation showing better hydration properties. In fact, the control formulation showed skin dehydration, which is not unusual for highly pigmented cosmetic formulations such as makeup and lipstick.

At seven hours after application, the average Novameter readings of the participants showed a reduction in skin hydration of approximately 4% below baseline on the areas with the hydrolysate formulation. A reduction in skin hydration of approximately 6% below baseline was observed on the areas with the control formulation. The hydration difference between the two makeup formulations after seven hours was approximately 2%, with the hydrolysate formulation continuing to show better hydration properties than the control formulation. Seven hours were required for the hydrolysate makeup formulation to approach the drying level to the skin as compared to the control makeup formulation.

Therefore, the incorporation of the hydrolysates according to the present invention into typically drying makeup formations shows improved skin hydration properties compared to formulations not containing the hydrolysates. In fact, the hydrolysate formulation appears to hydrate the skin initially, as opposed to the dehydrating effect seen in the control makeup formulation.

EXAMPLE 3

Enhanced Performance/Substantivity

Four different products for the treatment of fly abatement with animals, such as horses, were obtained (Ceratex, Gnat-Away, Solitude, and AquaPel). Concentrated versions of these products were not available; therefore commercially available dilutions were used.

To each sample, either water or the hydrolysate according to the present invention was added, to make a 10% hydrolysate containing solution. All formulations were thoroughly mixed with a stirrer until homogeneous. All formulations were transferred into spray bottles.

Four horses were selected to participate. The left side of each horse was sprayed with the control formulation. The right side of each horse was sprayed with the hydrolysate formulation. For eight (8) days, the number of flies on each horse's leg prior to re-application of any formulation was determined. With each of the four hydrolysate formulations, the cumulative effect after eight days demonstrated a significant decrease in fly count. FIGS. 3-7 clearly show that the hydrolysate formulation produces a greater decrease in fly count than the control formulation. Thus, the inclusion of the hydrolysate according to the present invention improves the cumulative performance of the active materials transferred with the hydrolysate in the commercially available fly abatement products.

The preferred embodiment(s) of the invention is described above in the Detailed Description of the Invention. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and representative description. It is not intended to be exhaustive or to limit the invention to the precise form disclosed, and many modifications and variations are possible in the light of the above teachings. The disclosed embodiments were chosen and described in order to best explain the principles of the invention and its practical application and to enable others skilled in the art to best utilize the invention in various other embodiments and with various modifications as are suited to the particular use contemplated.

What is claimed is:

1. A method for enhancing substantivity of a cosmetic or pharmaceutical composition for topical application to skin, comprising adding to the composition an effective amount of saponified jojoba oil, wherein the saponified jojoba oil comprises:
   a non-polar unsaponifiable fraction; and
   a polar hydrolphilic salt fraction;
   wherein the non-polar unsaponifiable fraction and the polar hydrophilic salt fraction correspond to the tandem reaction products of saponification of jojoba oil; and
   wherein a combination of the cosmetic or pharmaceutical composition and the effective amount of the saponified jojoba oil has increased substantivity compared to the cosmetic or pharmaceutical composition without the effective amount of the saponified jojoba oil.

2. The method of claim 1, wherein the saponified jojoba oil is comprised of:
   about 10-55 weight percent nonpolar unsaponifiable fraction (jojoba alcohols), and
   about 45-90 weight percent polar hydrophilic salt fraction.

3. The method of claim 1, wherein the saponified jojoba oil is comprised of:
   about 55 weight percent nonpolar unsaponifiable fraction (jojoba alcohols), and
   about 45 weight percent polar hydrophilic salt fraction.

4. The method of claim 1, wherein the composition is a skin hydrating agent.

5. The method of claim 1, wherein the saponified jojoba oil is comprised of:
   about 10-55*l* weight percent nonpolar unsaponifiable fraction (*jojoba alcohols*),
   about 45-90 weight percent polar hydrophilic salt fraction, and
   a residual amount of unsaponified jojoba oil.

6. The method of claim 1, wherein the saponified jojoba oil is comprised of:
   about 55 weight percent nonpolar unsaponifiable fraction (jojoba alcohols),
   about 45 weight percent polar hydrophilic salt fraction, and
   a residual amount of unsaponified jojoba oil.

7. The method of claim 1, wherein the composition is selected from the group consisting of: emollients, skin hydrating agents, lipstick, shampoos, conditioners, hair sheens, repellants, makeup, insect repellants, sun block, sunscreens, and tanning formulations.

* * * * *